United States Patent
Maliverney et al.

(10) Patent No.: US 9,499,643 B2
(45) Date of Patent: Nov. 22, 2016

(54) METHOD FOR PREPARING CARBENE IN SOLUTION, NOVEL STABLE FORM OF CARBENE OBTAINED IN PARTICULAR BY MEANS OF SAID METHOD, AND USES THEREOF IN CATALYSIS

(75) Inventors: Christian Maliverney, Saint Julien sur Bibost (FR); Laurent Saint-Jalmes, Vourles (FR); Sophie Gojon, Rueil-Malmaison (FR); Tsuyoshi Kato, Toulouse (FR); Antoine J. Baceiredo, Toulouse (FR)

(73) Assignees: Bluestar Silicones France SAS, Lyons (FR); C.N.R.S., Paris (FR)

( * ) Notice: Subject to any disclaimer, the term of this patent is extended or adjusted under 35 U.S.C. 154(b) by 524 days.

(21) Appl. No.: 13/520,834

(22) PCT Filed: Jan. 7, 2011

(86) PCT No.: PCT/EP2011/050175
§ 371 (c)(1),
(2), (4) Date: Mar. 5, 2013

(87) PCT Pub. No.: WO2011/083146
PCT Pub. Date: Jul. 14, 2011

(65) Prior Publication Data
US 2013/0158274 A1    Jun. 20, 2013

(30) Foreign Application Priority Data

Jan. 8, 2010   (FR) ..................................... 10 50108

(51) Int. Cl.
*C07D 233/58*   (2006.01)
*C08F 4/80*     (2006.01)
*C07D 233/06*   (2006.01)
*C08F 4/00*     (2006.01)

(52) U.S. Cl.
CPC ............... *C08F 4/80* (2013.01); *C07D 233/06* (2013.01); *C07D 233/58* (2013.01); *C08F 4/00* (2013.01)

(58) Field of Classification Search
CPC .................................................. C07D 233/58
See application file for complete search history.

(56) References Cited

FOREIGN PATENT DOCUMENTS

| EP | 0971941 A1 | 1/2000 |
| EP | 1268440 A1 | 1/2003 |
| FR | 2864543 A1 | 7/2005 |
| FR | 2900153 A1 | 10/2007 |
| WO | 02/098971 A1 | 12/2002 |

OTHER PUBLICATIONS

Todose, 2006, J. Organometallic Chemistry, vol. 691, p. 5356-5365.*
Nolan, Coordination Chemistry Reviews, 2009, vol. 253, p. 862-892.*
Chen, H., Justes, D. R., & Cooks, R. G. "Proton affinities of N-heterocyclic carbene super bases", (2005) Organic letters, 7(18), 3949-3952.
Knishevitsky, A. V. et al. "Copper (I) halide complexes of the new 4, 4'-bridged heteroaromatic biscarbenes of the 1, 2, 4-triazole series", Journal of Organometallic Chemistry, (2008), 693(8) 1405-1411.
Shi, J. C. "Synthesis of chiral imidazolinium carbene from a carbohydrate and its rhodium (I) complex", (2007), European Journal of Inorganic Chemistry, (15), 2221-2224.
Scholl, M. Synthesis and Activity of a New Generation of Ruthenium-Based Olefin Metathesis Catalysts Coordinated with 1, 3-Dimesityl-4, 5-dihydroimidazol-2-ylidene Ligands §, (1999) Organic Letters, 1(6), 953-956.
International Search Report for PCT/EP2011/050175 Mailed Apr. 5, 2011.

* cited by examiner

*Primary Examiner* — Michael Barker
*Assistant Examiner* — Karen Cheng
(74) *Attorney, Agent, or Firm* — McBee Moore Woodward Vanik IP LLC (57) ABSTRACT

The invention relates to a method for preparing carbene by means of deprotonation of a precursor salt using a strong base. A purpose of the invention is to enhance the synthesis of carbenes, i.e. to simplify same, to make said synthesis more economical and to obtain a liquid or solid, stable and pure form constituting a catalytic system that is easy to store and use and that has a higher efficiency, higher yield and higher selectivity than carbene catalysts of the prior art. In order to do so, the method comprises deprotonation in a solvent including an alcohol. The invention also relates to an alcohol-containing solution and carbene, and to a solid that can be obtained from the solution, e.g. by means of sublimation.

16 Claims, 2 Drawing Sheets

METHOD FOR PREPARING CARBENE IN SOLUTION, NOVEL STABLE FORM OF CARBENE OBTAINED IN PARTICULAR BY MEANS OF SAID METHOD, AND USES THEREOF IN CATALYSIS

CROSS REFERENCE TO RELATED APPLICATIONS

This application is a §371 National Stage Application of PCT/EP2011/050175, filed Jan. 7, 2011, which claims priority to French Application No. 1050108, filed Jan. 8, 2010.

BACKGROUND OF THE INVENTION

Field of the Invention

The field of the invention is that of the synthesis of carbenes and of their applications, in particular as catalysts or ligands, in:

- the preparation of PolyOrganoSiloxanes (POS) by polymerization by ring opening and/or by redistribution and/or polycondensation of POS,
- the hydrosilylation of at least one PolyOrganoSiloxane -A- (POS) carrying ethylenic and/or acetylenic unsaturation(s), using at least one polyorganohydrosiloxane -B-, or of other ethylenically and/or acetylenically unsaturated compounds,
- hydrogenation,
- olefin metathesis,
- C—C and/or C—N cross coupling,
- asymmetric or enantioselective synthesis,
- or organic synthesis: esterification reactions, transesterification reactions, condensation reactions of aldol type, for example.

The present invention relates to a process for the preparation of carbene by deprotonation of a precursor salt using a strong base.

Throughout the present account, any singular denotes without distinction a singular or a plural.

Description of Related Art

Platinum/carbene complexes are known as catalysts for the hydrosilylation of PolyOrganoSiloxane (POS) comprising ≡Si-vinyl units by means of POS comprising ≡Si—H units. Mention may be made, by way of example, of application PCT WO-A-02/098971, which describes a silicone composition which can be crosslinked to give an elastomer by hydrosilylation in the presence of platinum catalysts formed by a complex C3 or C4:

(C3)

(C4)

The carbenes of use as ligands for catalytic metals are made use of in other fields than that of silicones. Thus, patent EP-B-0 971 941 describes catalysts based on Ruthenium and Osmium/carbene complexes for the thermal metathesis of cycloolefins.

In addition, a paper by J. L. Hedrick et al. which appeared in 2002 (JACS, 124, No. 6, pp. 914-915, 2002) teaches that N-heterocyclic carbenes can be used as catalysts for the polymerization of cyclic esters. More specifically, 1,3-bis (2,4,6-trimethylphenyl)imidazol-2-ylidene was tested as catalyst for the polymerization of L-lactide, ε-caprolactone and β-butyrolactone in the presence of an alcohol used as initiator.

A more recent and fuller paper (cf. JACS, 125, No. 10, pp. 3046-3056, 2003) describes the preparation of carbene in situ in order to avoid the problems of hydrolysis. The promoters used are of thiazolium, imidazolium and imidazolinium type, respectively giving thiazolecarbene, imidazole-2-ylidenecarbene and imidazolin-2-ylidenecarbene catalysts, when they are brought into the presence of potassium tert-butoxide. Patent application FR-2864543-A discloses carbenes obtained by deprotonation of an imidazolium salt in the presence of a strong base and used for the synthesis of polyorganosiloxane silicones, by polymerization by ring opening and/or redistribution of linear or cyclic polyorganosiloxanes.

Patent application FR-2900153-A discloses a carbene, dicyclohexyldiaminocarbene, obtained by deprotonation of the corresponding imidazolium triflate:

according to the following procedure:

This carbene catalyzes the polycondensation of silanols of the silicone oil type of formula $[(CH_3)_2(OH)SiO_{1/2}]$—$[(CH_3)_2SiO_{2/2}]_{10}$—$[(CH_3)_2(OH)SiO_{1/2}]$.

These carbenes of NHC type, obtained by deprotonation of an imidazolium salt using a strong base in a solvent of

THF type, are subsequently isolated by filtration, in order to remove the salt formed, followed by recrystallization, indeed even sublimation.

In this respect, patent EP-1 268 440-B1 relates to a process for the preparation of N-heterocyclic carbenes which comprises the heating of a dialkylimidazolium halide with a strong base under reduced pressure. The carbene is distilled during its formation with a horizontal distillation device, optionally distilled with the same device a second time. It can be isolated pure under inert gas or dissolved in an inert solvent (preferably an aromatic solvent).

This process cannot be operated industrially as the horizontal distillation, which uses a laboratory device, is only possible from a few grams to a few tens of grams. Furthermore, the carbene, isolated pure or in inert solvent, is highly sensitive to oxygen and to the slightest trace of moisture and for this reason has a limited lifetime.

These carbenes are highly reactive entities which decompose in the open air, which implies storing them and handling them under an inert atmosphere (argon or nitrogen). Their synthesis is itself also very obviously carried out under an inert atmosphere and the solvent used is dried and freshly distilled beforehand.

Furthermore, the paper by M. A. Schmidt et al., *Tetrahedron Letters* 49 (2008), 4316-4318, discloses the interaction of N,N'-bismesitylimidazolium-2-yl and alcohols in the presence of benzene:

From this observation, the authors deduce that the stabilizing effect of these interactions can be used for the storage of nitrogenous heterocyclic carbenes, since the removal of the volatiles releases these nitrogenous heterocyclic carbenes. In the case where the alcohol is methanol, this evaporation of the volatiles has to be accompanied by a desolvation in order to restore the carbene-alcohol complex.

In view of this state of the art, the invention is targeted at satisfying at least one of the following essential objectives:

to improve the synthesis of carbenes, that is to say simplifying it, rendering it more economical and resulting in a pure stable solid or liquid form which constitutes a catalytic system which is easy to store and to use and which is also more effective, more profitable and more selective than the carbene catalysts of the prior art;

to obtain carbenes in solution which are stable in the open air for at least several months;

to provide novel metal complexes of carbene which are stable, economical and highly effective catalytically;

to provide processes and catalysts which are stable, economical and highly effective for:
  a. preparation of PolyOrganoSiloxanes (POS) by polymerization by ring opening and/or by redistribution/polycondensation of POS
  b. hydrosilylation of at least one PolyOrganoSiloxane -A- (POS) carrying ethylenic and/or acetylenic unsaturation(s), using at least one polyorganohydrosiloxane -B-, or of other ethylenically and/or acetylenically unsaturated compounds
  c. hydrogenation
  d. olefin metathesis
  e. C—C and/or C—N cross coupling
  f. enantioselective synthesis
  g. organic synthesis to provide processes a to g having better conversion yields;

to provide a carbene-based catalytic system which is highly effective, which exhibits at least one of the following characteristics:
  soluble in silicone oils and in particular silicone gums;
  simple and relatively inexpensive to synthesize;
  stable;
  having good resistance to hydrolysis; and which makes it possible:
  to polymerize silicones under mild conditions (low temperatures≤100° C.);
  to reduce the reaction times, in particular for the preparation of viscous oils and of gums;
  to reduce, indeed even to eliminate, residues of catalyst and of its derivatives in the final polymer, in order to prepare silicone polymers of high viscosity and of improved thermal resistance, this being achieved in a profitable manner;
  to functionalize a whole POS palette;
  to improve the polydispersity of the polymers formed and to favor the formation of linear structures in comparison with cyclic oligomers;
  to easily remove possible catalyst residues;
  to favor the formation of linear silicone polymers in comparison with the formation of cyclic polymers;
  to guarantee high reproducibility;
  and to limit the sensitivity to the variability in the starting materials.

SUMMARY

These objectives, among others, are achieved by the present invention, which relates, first of all, to a process for the preparation of a catalyst or of a reactant comprising a carbene and stable at 20° C. which is provided in the form of a solution A composed of at least one alcohol and at least one carbene comprising the following stages:

at least one strong base, optionally generated in situ, is reacted, preferably at a temperature of between 0° C. and 100° C., with at least one compound B which is the precursor of a carbene C, said compound B, which is a salt, comprising an iminium functional group of the following structure (I):

with:
X being chosen from the group consisting of: O, S, —N(R) and —P(R), with R being a $C_1$-$C_{30}$ group,
$R_1$, $R_2$ and $R_3$ being identical or different $C_1$-$C_{30}$ groups which are optionally substituted and which optionally comprise one or more atoms chosen from the group consisting of: S, P, Si, N and O,
X, $R_1$, $R_2$ and $R_3$, taken in pairs, can form a 5-, 6- or 7-membered ring;
with as following conditions:
the choice of the strong base is made so as to be able to carry out a deprotonation of the hydrogen of the iminium functional group of structure (I), and
the reaction is carried out in a solvent which is an alcohol or an alcohol mixture.

DETAILED DESCRIPTION OF A PREFERRED EMBODIMENT

Advantageously, this deprotonation is carried out at ambient temperature (20° C.). It is to the credit of the inventors to have risked the synthesis of carbene in an alcoholic medium despite the existing preconception with regard to carbene-water or alcohol incompatibility. This has made it possible, entirely surprisingly and unexpectedly, to overcome the burdensome constraint of employing an anhydrous reaction medium and of isolating the carbene by sublimation with very low yields (<40% by weight).

The process according to the invention is much simpler since the purification operations are reduced, indeed even eliminated. It is also more economical. In short, it is a much more industrial process than the known processes.

Preferably, the compound B is chosen from the compounds of following general formula (III) or (III'):

in which:
A and B independently represent C or N, it being understood that:
in the formula (III), when A represents N, then $T_4$ is not present and, when B represents N, then $T_3$ is not present;
in the formula (III'), when A represents N, then $T_4$ or $T_{4'}$ is not present and, when B represents N, then $T_3$ or $T_{3'}$ is not present;
$T_3$, $T_{3'}$, $T_4$ and $T_{4'}$ independently represent a hydrogen atom; an alkyl group; a cycloalkyl group optionally substituted by an alkyl or alkoxy group; an aryl group optionally substituted by an alkyl or alkoxy group; an alkenyl group; an alkynyl group; or an arylalkyl group in which the aryl part is optionally substituted by an alkyl or alkoxy group; or else
$T_3$ and $T_4$ can form, together and with A and B when the latter each represent a carbon atom, an aryl, it being understood that, in this case, $T_{3'}$ and $T_{4'}$ are not present;
$T_1$ and $T_2$ independently represent an alkyl group; an alkyl group optionally substituted by an alkyl; an alkyl group which is perfluorinated or optionally substituted by a perfluoroalkyl group; a cycloalkyl group optionally substituted by an alkyl or alkoxy group; an aryl group optionally substituted by an alkyl or alkoxy group; an alkenyl group; an alkynyl group; or an arylalkyl group in which the aryl part is optionally substituted by an alkyl or alkoxy group; or else
$T_1$ and $T_2$ independently represent a monovalent radical of following formula (III):

$$—V1-V2 \qquad (III)$$

in which:
V1 is a saturated or unsaturated divalent hydrocarbon group, preferably a linear or branched $C_1$-$C_{10}$ alkylene, which is optionally substituted,
V2 is a monovalent group chosen from the group of the following substituents:
alkoxy, —$OR^a$, with $R^a$ corresponding to hydrogen, alkyl or aryl;
silyl, —$Si(OR^b)_x(R^c)_{3-x}$, with $R^b$ corresponding to hydrogen, alkyl, silyl or siloxanyl, $R^c$ corresponding to alkyl, aryl and x being an integer between 0 and 3;
amine, preferably —$N(R^a)_2$, with $R^a$ corresponding to hydrogen, alkyl or aryl; or alternatively;
the substituents $T_1$, $T_2$, $T_3$, $T_{3'}$, $T_4$ and $T_{4'}$ can form, in pairs, when they are located on two adjacent ring members in the formulae (III) and (III'), a saturated or unsaturated hydrocarbon chain;
$Z_1$ independently represents an anion derived from a Brönsted acid (protic acid) preferably chosen from the group consisting of:
carboxylic acids of formula $G_o$-COOH, in which $G_o$ represents an alkyl and advantageously a $C_1$-$C_{22}$ alkyl; or an aryl, advantageously a $C_6$-$C_{18}$ aryl, optionally substituted by one or more $C_1$-$C_6$ alkyls;
sulfonic acids of formula $G_o$-$SO_3H$, in which $G_o$ is as defined above;
phosphoric acids of formula $G_o$-$PO_3H$, in which $G_o$ is as defined above;
the following inorganic acids: HF, HCl, HBr, HI, $H_2SO_4$, $H_3PO_4$, $HClO_4$ and $HBF_4$, taken by themselves alone or in combination with one another;
and their mixtures.

As regards the salt (III), the $Z_1^-$ anion is the anion derived from an organic or inorganic Brönsted acid (protic acid). Usually, the anion $Z_1^-$ is derived from an acid exhibiting a pKa of less than 6. Preferably, $Z_1^-$ derives from an acid with a pKa of less than 4, better still of less than 2. The pKa values concerned here are the pKa values of the acids as measured in water.

Examples of acids are carboxylic acids of formula: $G_o$-COOH, in which $G_o$ represents alkyl and for example ($C_1$-$C_{22}$)alkyl; or else aryl and for example ($C_6$-$C_{18}$) aryl optionally substituted by one or more alkyls, preferably one or more ($C_1$-$C_6$)alkyls; sulfonic acids of formula: $G_o$-$SO_3H$, in which $G_o$ is as defined above; and phosphonic acids of formula: $G_o$-$PO_3H$, in which $G_o$ is as defined above; other acids are HF, HCl, HBr, HI, $H_2SO_4$, $H_3PO_4$, $HClO_4$ and $HBF_4$.

Preferred examples of carboxylic acids are acetic acid, benzoic acid and stearic acid. Mention will be made, as preferred sulfonic acid, of benzenesulfonic acid and mention will be made, as preferred phosphonic acid, of phenylphosphonic acid.

According to the invention, preference is more particularly given to the $Z_1^-$ anions derived from the acids HCl, HI, $HBF_4$ and $HPF_6$.

Thus, $Z_1^-$ anions which are particularly preferred according to the invention are the halide and tetrafluoroborate and hexafluorophosphate anions.

A few examples of imidazolium salts are given below.

These consumables are either commercially available or are easily prepared by a person skilled in the art from commercially available compounds.

A method for the synthesis of the salts of formula (III) in which A=B=C is described in U.S. Pat. No. 5,077,414.

This process comprises the reaction:
of an α-dicarbonyl compound of following formula (X):

X in which $T_3$ and $T_4$ are as defined above,
with HCHO and two amines of formulae $T_1$-$NH_2$ and $T_2$-$NH_2$, in the presence of an appropriate acid.

The nature of the $Z_1$ anion in the salts of formula (III) depends on the acid used in this stage. The acids which can be used are, for example, those listed above and those from which $Z_1$ derives.

Other methods for the preparation of the salts of formula (III) are provided in Chem. Eur. J., 1996, 2, No. 12, pages 1627-1636, and Angew. Chem. Int. Ed. Engl., 1997, 36, 2162-2187.

Preferably, the alcohol corresponds to the formula (I°) R°OH, in which R° corresponds to an alkyl, cycloalkyl, aryl, alkenyl, alkynyl, arylalkyl, silyl or siloxane group, R° preferably being chosen from the group consisting of: methyl, ethyl, propyl and butyl. In a noteworthy manner, the strong base is chosen from the group of the alkali metal and alkaline earth metal hydroxides, alkoxides, hydrides and amides, preferably from the subgroup consisting of: $CH_3ONa$, potassium tert-butoxide, KOH, NaOH, $CH_3CH_2OMgOCH_2CH_3$ and their mixtures.

According to one possibility, this strong base can be formed in situ, for example by the addition of sodium or sodium hydride or magnesium to the alcohol under consideration. Thus it is that the alkoxides can be generated in situ.

Advantageously, the deprotonation produces a salt which precipitates and which is separated from the solution A.

Preferably, the solvent is sublimed so as to collect the carbene C in the solid form.

The invention also relates to a solution A, in particular obtained by the process as described above, characterized in that it is based on alcohol and on at least one carbene C of formula:

with:
X being chosen from the group consisting of: O, S, —N(R) and —P(R), with R being a $C_1$-$C_{30}$ group,
$R_1$, $R_2$ and $R_3$ being identical or different $C_1$-$C_{30}$ groups which are optionally substituted and which optionally comprise one or more atoms chosen from the group consisting of: S, P, Si, N and O, and
X, $R_1$, $R_2$ and $R_3$, taken in pairs, can form a 5-, 6- or 7-membered ring.

Preferably, the carbene C has the formula (II) or (II'):

in which:
A and B independently represent C or N, it being understood that:
in the formula (II), when A represents N, then $T_4$ is not present and, when B represents N, then $T_3$ is not present;
in the formula (II'), when A represents N, then $T_4$ or $T_{4'}$ is not present and, when B represents N, then $T_3$ or $T_{3'}$ is not present;
$T_3$, $T_{3'}$, $T_4$ and $T_{4'}$ independently represent a hydrogen atom; an alkyl group; a cycloalkyl group optionally substituted by alkyl or alkoxy; an aryl group optionally substituted by alkyl or alkoxy; an alkenyl group; an alkynyl group; or an arylalkyl group in which the aryl part is optionally substituted by alkyl or alkoxy; or else
$T_3$ and $T_4$ can form, together with A and B when the latter each represent a carbon atom, an aryl, it being understood that, in this case, $T_{3'}$ and $T_{4'}$ are not present;

T₁ and T₂ independently represent an alkyl group; an alkyl group optionally substituted by alkyl; an alkyl group which is perfluorinated or optionally substituted by a perfluoroalkyl group; a cycloalkyl group optionally substituted by alkyl or alkoxy; an aryl group optionally substituted by alkyl or alkoxy; an alkenyl group; an alkynyl group; or an arylalkyl group in which the aryl part is optionally substituted by alkyl or alkoxy; or else T₁ and T₂ independently represent a monovalent radical of following formula (III):

$$—V1-V2 \quad (III)$$

in which:
   V1 is a saturated or unsaturated divalent hydrocarbon group, preferably a linear or branched alkylene, which is optionally substituted,
   V2 is a monovalent group chosen from the group of the following substituents:
      alkoxy, —OR$^a$, with R$^a$ corresponding to hydrogen, alkyl or aryl;
      silyl, —Si(OR$^b$)$_x$(R$^c$)$_{3-x}$, with R$^b$ corresponding to hydrogen, alkyl, silyl or siloxanyl, R$^c$ corresponding to alkyl, aryl and x being an integer between 0 and 3;
      amine, preferably —N(R$^a$)$_2$, with R$^a$ corresponding to hydrogen, alkyl or aryl; or alternatively;
   the substituents T₁, T₂, T₃, T₃', T₄ and T₄' can form, in pairs, when they are located on two adjacent ring members in the formulae (II) and (II'), a saturated or unsaturated hydrocarbon chain.

The term "alkyl" denotes a saturated and linear or branched hydrocarbon chain which is optionally substituted (e.g., by one or more alkyls) and which preferably has from 1 to 10 carbon atoms, for example from 1 to 8 carbon atoms, better still from 1 to 7 carbon atoms.

Examples of alkyl groups are in particular methyl, ethyl, isopropyl, n-propyl, tert-butyl, isobutyl, n-butyl, n-pentyl, isoamyl and 1,1-dimethylpropyl.

The alkyl part of the alkoxy group is as defined above. The alkyl group which is perfluorinated or optionally substituted by a perfluoroalkyl group preferably corresponds to the formula:

$$—(CH_2)_p—C_qF_{2q+1}$$

in which p represents 0, 1, 2, 3 or 4, q is an integer from 1 to 10 and $C_qF_{2q+1}$ is linear or branched. Preferred examples of this group are: —(CH₂)₂—(CF₂)₅—CF₃ and —(CF₂)₇—CF₃.

The expression "aryl" denotes an aromatic hydrocarbon group which has from 6 to 18 carbon atoms and which is monocyclic or polycyclic and preferably monocyclic or bicyclic. It should be understood that, in the context of the invention, the term "polycyclic aromatic group" is understood to mean a group exhibiting two or more aromatic nuclei fused (ortho-fused or ortho- and peri-fused) to one another, that is to say exhibiting, in pairs, at least two carbons in common.

Said aromatic hydrocarbon ("aryl") group is optionally substituted, for example, by one or more C₁-C₃ alkyls, one or more halogenated hydrocarbon (e.g., CF₃) groups, one or more alkoxys (e.g., CH₃O) or one or more hydrocarbon groups comprising one or more ketone units (e.g., CH₃CO—).

Mention may be made, as an example of aryl, of the phenyl, naphthyl, anthryl and phenanthryl radicals.

The expression "arylalkyl" denotes an alkyl group as defined above substituted by one or more aryl groups on its hydrocarbon chain, the aryl group being as defined above. Examples thereof are benzyl and triphenylmethyl.

The term "cycloalkyl" is understood to mean a saturated and mono- or polycyclic, preferably mono- or bicyclic, hydrocarbon group preferably exhibiting from 3 to 10 carbon atoms, better still from 3 to 8 carbon atoms. The term "saturated polycyclic hydrocarbon group" is understood to mean a group exhibiting two or more cyclic nuclei attached to one another via σ bonds and/or fused in pairs.

Examples of polycyclic cycloalkyl groups are adamantane and norbornane.

Examples of monocyclic cycloalkyl groups are cyclopropyl, cyclobutyl, cyclopentyl, cyclohexyl, cycloheptyl and cyclooctyl.

The term "alkenyl" is understood to mean an unsaturated and linear or branched hydrocarbon chain which is substituted or unsubstituted and which exhibits at least one olefinic double bond, more preferably a single double bond. Preferably, the alkenyl group exhibits from 2 to 8 carbon atoms, better still from 2 to 6 carbon atoms. This hydrocarbon chain optionally comprises at least one heteroatom, such as O, N or S. Preferred examples of alkenyl groups are the allyl and homoallyl groups.

The term "alkynyl" is understood to mean, according to the invention, an unsaturated and linear or branched hydrocarbon chain which is substituted or unsubstituted and which exhibits at least one acetylenic triple bond, more preferably a single triple bond. Preferably, the alkynyl group exhibits from 2 to 8 carbon atoms or better still from 2 to 6 carbon atoms. Mention may be made, by way of example, of the acetylenyl group and the propargyl group. This hydrocarbon chain optionally comprises at least one heteroatom, such as O, N or S.

The term "silyl" is understood to mean, according to the invention, a linear or branched group comprising at least one silicon atom. Polydimethylsiloxane chains are examples of silyl groups.

The carbenes of formulae (II) and (II') can exhibit at least two fused nuclei, that is to say that at least two groups from T₁, T₂, T₃, T₃', T₄ and T₄' located on two adjacent ring members together form a saturated or unsaturated hydrocarbon chain preferably exhibiting from 3 to 6 carbon atoms. The term "saturated or unsaturated hydrocarbon chain" is understood to mean a linear or branched hydrocarbon chain which may or may not exhibit one or more unsaturations of olefinic double bond or acetylenic triple bond type.

As regards preferred embodiments in the formula (II) or (II'), these are forms in which A=B=carbon atom in the formula (II) given above.

Preferred meanings for T₁ and T₂ in this formula (II) are:
   alkyl, in particular n-propyl, n-pentyl or neopentyl (—CH₂—C(CH₃)₃);
   cycloalkyl, in particular cyclopentyl, cyclohexyl or adamantyl;
   alkenyl, in particular allyl (—CH₂—CH=CH₂) or methallyl (—CH₂—C(CH₃)=CH₂);
   alkynyl, in particular propargyl or homopropargyl (—(CH₂)₂—C≡CH);
   or monovalent group (V) defined above, in particular:

Still in the formula (II) and preferably, $T_3$ and $T_4$ both correspond to hydrogen or together form an aryl, better still a phenyl.

Mention may be made, as examples of carbenes, of those described in table 2, page 48, of the publication "Bourissou et al., *Chem. Rev.*, 2000, 100, 39-91". This table 2, page 48, is included by way of reference in the present account.

In accordance with the invention, the carbene(s):
is (are) prepared separately,
and/or is (are) generated in situ from at least one precursor.

The Novel Liquid or Solid Form of Carbene

The process according to the invention thus gives access to a solution based on alcohol and carbene. Surprisingly and unexpectedly, this alcoholic solution is stable and catalytic.

The invention also covers this stable and catalytic alcoholic solution of carbene per se, obtained by the process according to the invention or by any other process.

The Applications

According to another of its aspects, the invention is targeted at a process for the preparation of PolyOrganoSiloxanes (POS) by polymerization by ring opening and/or by redistribution of POS and/or by polycondensation, in the presence of a catalyst (C) comprising at least one carbene as obtained by the process as defined above, said carbene being provided in the form of an alcoholic solution or of a solid extracted from said liquid.

Within the meaning of the invention, the "polymerization by ring opening" corresponds to a polymerization in which a cyclic compound (monomer) is opened in order to form a linear polymer.

Within the meaning of the invention, the "polymerization by redistribution" corresponds to a term as accepted by a person skilled in the art in the chemistry of silicones. In particular, the "polymerization by redistribution" is understood, in the field of silicones, as a rearrangement of organosiloxanes having different structures and/or molar masses. This rearrangement results in a single new POS.

The invention opens new routes in the catalysis of:
the preparation of PolyOrganoSiloxanes (POS) by polymerization by ring opening and/or by redistribution and/or polycondensation of POS;
the hydrosilylation of at least one PolyOrganoSiloxane -A- (POS) carrying ethylenic and/or acetylenic unsaturation(s), using at least one polyorganohydrosiloxane -B-, or of other ethylenically and/or acetylenically unsaturated compounds;
hydrogenation;
olefin metathesis;
C—C and/or C—N cross coupling;
asymmetric or enantioselective synthesis;
or organic synthesis: esterification reactions, transesterification reactions, condensation reactions of aldol type, for example.

These routes are highly effective in terms of storage and of handling, of ease of use of the carbene catalyst and in terms of catalytic activity, of selectivity (better degrees of conversion and yields), of ease of use (low temperature, little or no purification), of obtaining POS having good polydispersity indices and which can have high viscosities, inter alia.

These performances are all the more advantageous as they go hand in hand with advantages in terms of cost, safety and non-ecotoxicity, in particular.

The examples which follow will make possible a better apprehension of the process and the liquid or solid carbene according to the invention, by bringing out all their advantages and the possible alternative embodiments.

General Points:

In the protocol according to the invention, use is made directly of an alcohol as solvent for the reaction, making possible the instantaneous protection of the carbene as soon as it is formed. The synthesis is carried out in the open air.

Synthesis of NHCs in an Alcohol

This synthesis of an NHC ($R^1$: tert-butyl) was tested under several conditions by varying the base used and the alcohol used. It emerges therefrom that the use of a solvent of ethanol or isopropanol type and of a base of tBuOK or KOH type makes it possible to obtain the carbene. Specifically, the NMR (proton and carbon) spectra of the solutions are identical to those obtained in the case of a mixture of pure carbene and of alcohol.

The factors which make it possible to attest to the formation of the carbene are in particular:
The absence of proton on the carbon located between the two nitrogen atoms ($^1$H NMR spectrum)
The presence of a signal at 130 ppm corresponding to a carbon of quaternary type ($^{13}$C NMR spectrum)

The process according to the invention thus made it possible to synthesize a novel carbene, normally too unstable to be isolated ($R^1$: methyl).

-A- Synthesis

Example A1

Synthesis of NHC-tBu by Deprotonation with tBuOK in Isopropanol 210 mg of tBuOK (1.87 mmol) are weighed out and are treated in the open air with a solution of 500 mg of imidazolium salt (1.87 mmol) in approximately 4 ml of isopropanol with stirring. A slight exotherm is observed in the first minutes. After stirring at ambient temperature for approximately 1 h, the KCl is removed by filtration on a sintered glass funnel and a slightly colored solution is obtained.

Figure 1:
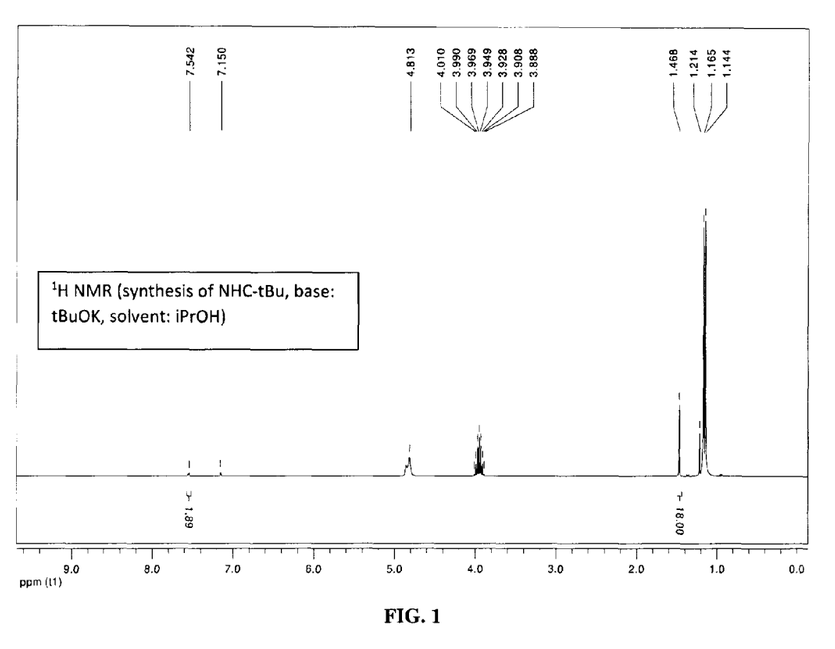
FIG. 1 shows the proton NMR spectrum of the solution obtained in Example A1.
Figure 2:
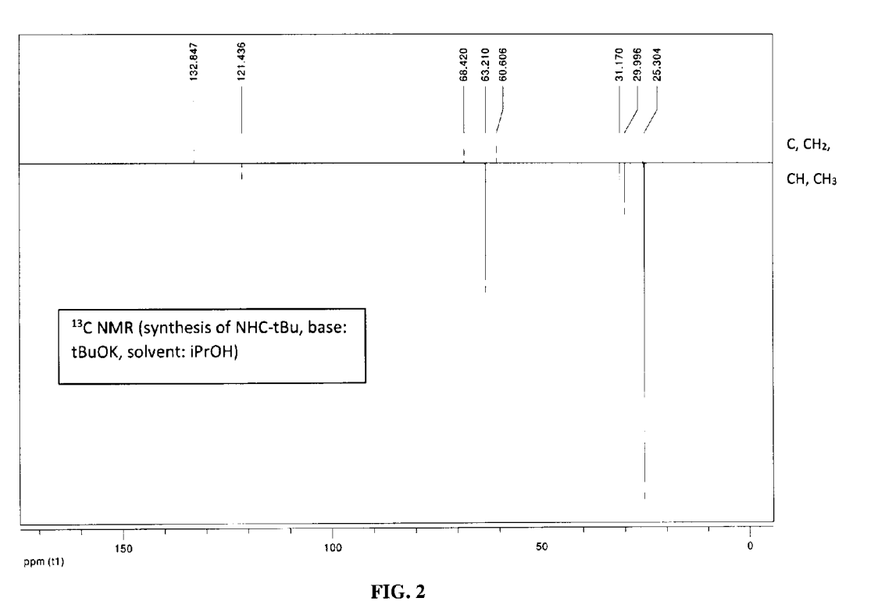
FIG. 2 shows the carbon NMR spectrum of the solution obtained in Example A1.

The NMR (proton and carbon) spectra of this solution are represented in FIG. 1 and FIG. 2.

Example A2

Synthesis of NHC-tBu by Deprotonation with KOH in Isopropanol 93 mg of KOH pellets (1.66 mmol) are weighed out and are dissolved in 2 ml of isopropanol, a few drops of distilled water being added in order to thoroughly dissolve. 450 mg of imidazolium salt (1.66 mmol) dissolved in 2 ml of isopropanol are subsequently added. A slight exotherm is observed in the first minutes. After stirring at ambient temperature for approximately 1 h, the mixture is filtered on a sintered glass funnel and a slightly colored solution is obtained.

| $^1$H NMR | $^{13}$C NMR (jmod) |
|---|---|
| 1.15 (iPrOH) | 25.3 (iPrOH) |
| 1.21 (tBuOH) | 30.0 (N—C—(C$\underline{H}_3$)$_3$) |
| 1.47 (s, 18H, N—C—C$\underline{H}_3$)$_3$) | 31.2 (tBuOH) |
| 3.95 (iPrOH) | 60.6 (N—$\underline{C}$—(CH$_3$)$_3$) |
| 4.81 (iPrOH) | 63.2 (iPrOH) |
| 7.15 (C$_6$D$_6$) | 68.4 (tBuOH) |
| 7.54 (s, 2H, N—C$\underline{H}$=C$\underline{H}$—N) | 121.4 (N—$\underline{C}$H=$\underline{C}$H—N) |
| | 132.8 (carbenic C) |

Example A3

Preparation of an Ethanolic Solution of the Carbene NHC-Cy2 (Cy=cyclohexyl)

20 ml of ethanol are added to a 50 ml round-bottomed flask containing 4 g of N,N'-dicyclohexylimidazolium tetrafluoroborate (12.5 mmol) and 1.4 g of potassium tert-butoxide (12.5 mmol) cooled to 0° C. After 10 min, the heterogeneous mixture is stirred at 20° C. for from one to two hours. The solid (KBF$_4$) is then filtered off and then rinsed with 6 ml of ethanol. The clear, slightly yellow filtrate is concentrated to give a carbene solution at 43.87% by weight of theory, used as is as catalyst or complexing agent. It is preferable to store this solution at ambient temperature (20° C.), it being possible for the carbene to crystallize under cold conditions. An inert gas is not necessary.

-B- Reactivity

B1 Hydrosilylation catalysts: platinum-carbene

B11 Synthesis of "platinum-carbene":

General Reaction:

Karstedt platinum
10.25% by weight
of Pt

MW = 613.84 (R = Cy)

Example B111

Synthesis from Dicyclohexylimidazolium Tetrafluoroborate (WO 02/98888 of 4 Jun. 2002)→Sample 1

The synthesis requires a reactor under an inert gas, anhydrous THF, toluene to precipitate most of the potassium salt, two filtrations; the productivity is low (13% w/w), the yield moderate (87%) and the isolated product generally contains salts (Pt assay=30.4% by weight for a theoretical value of 31.8% by weight).

Example B112

Synthesis in a THF-Diluted Medium According to the Invention (Dilution Equal to 1)→Sample 2

10 g of Karsted platinum comprising 10.25% by weight of platinum (5.25 mmol) and 10 ml of THF are placed in a 50 ml single-necked round-bottomed flask. 3.06 g of the solution of NHC-Cy2 carbene described in A3 (5.78 mmol) are added with stirring to the solution obtained. After 2 h at 20° C., the solution is evaporated, the greasy solid is taken up in 20 ml of isopropanol, the suspension is filtered and the solid is dried under vacuum: 2.8 g obtained, i.e. yield of 87.5%.

Elem. anal.: 31.01% Pt

→nonoptimized yield the same, purer product, highly simplified process.

Example B113

Solvent-Free Synthesis Sample 3

Same procedure as above without THF: addition of the carbene solution to the Karsted platinum, precipitation after stirring for 10 min. After 2 h, 20 ml of isopropanol are added. The white solid is filtered off, rinsed with 5 ml of the same solvent and dried under vacuum: 2.75 g obtained, i.e. 86% yield.

Elem. anal.: 31.43% Pt

→nonoptimized yield the same, even purer product, more simplified process.

Example B114

Same Reaction as B112 (with THF) with a Carbene Solution Prepared One Month Previously and Stored Without Precautions at 20° C.→sample 4

2.8 g obtained, i.e. yield of 87.5%.

Elem. anal.: 31.51% Pt

→nonoptimized yield the same, even purer product, robust and simple process.

Example B115

Preparation of Platinum-Carbene with Carbene=NHC-tBu2

Same procedure as in example B112, with a 37.8% by weight ethanolic solution of NHC-tBu2 carbene (2.76 g for 5.78 mmol). Achievement of 2.6 g of a fine white solid, i.e. 88% yield.

Elem. anal.: 34.56% Pt (th. 34.73%).

Example B12

Tests on the Catalysts

The reaction studied is the solvent-free hydrosilylation of 1-octene by 1,1,1,2,3,3,3-heptamethyltrisiloxane:

10 g of octene (89.1 mmol, 1.2 eq.) are placed in a 50 ml three-necked round-bottomed flask. The round-bottomed flask is heated to a set temperature of 85° C. 27 μl of 2.7% solution of platinum-carbene in xylene ($1.1 \times 10^{-3}$ mol %/octene) are added and the hydrosiloxane is added over 1 h 30 using a syringe driver. The disappearance of the hydrosiloxane is monitored over time by gas analysis. The results for conversion of the hydrosilane are given in the following table:

| Pt-carbene | SiH conversion after running in 20% | SiH conversion after running in 50% | SiH conversion after running in 100% | 1 h 30 after running in has been completed |
|---|---|---|---|---|
| Sample 1 | 11.0% | 76.0% | 90.0% | 99.7% |
| Sample 2 | 8.3% | 70.0% | 91.0% | 99.5% |
| Sample 3 | 10.0% | 75.0% | 92.0% | 99.7% |
| Sample 4 | 16.7% | 78.0% | 91.0% | 99.8% |

It is deduced therefrom that all the catalysts are equivalent overall.

Example B13

The stability in solution of an NHC-di(tert-butyl) carbene (NHC-tBu2, prepared in example B115) is evaluated:
a) Comparative, in THF and under an ambient air atmosphere after:
  3 h: 0% decomposition,
  20 h: 2% decomposition,
  48 h: 25% decomposition,
  7 days: 100% decomposition
b) Invention, in solution (40% by weight) in MeOH, EtOH or iPrOH:
  after 1 year, no decomposition.

The invention claimed is:

1. A process for preparing a catalyst and/or a reactant, the reactant and catalyst comprising at least one carbene C in the form of a solution A that is stable at 20° C., wherein the solution A comprises at least one alcohol and the at least one carbene C,
  wherein said process comprises:
  reacting at least one strong base, optionally generated in situ, with at least one compound B, which is a precursor of the at least one carbene C,
  wherein
    the at least one strong base deprotonates an iminium functional group of structure (III) or (III'), and
    wherein the deprotonating is carried out in an alcoholic medium, comprising the at least one alcohol, and said deprotonating produces a salt, which precipitates in and is separated from said solution A;
  and wherein said compound B is selected from the group consisting of one or more compounds of formula (III) and (III'):

wherein
  A and B are independently C or N, wherein
    in formula (III), when A is N, then $T_4$ is not present and, when B is N, then $T_3$ is not present;
    in formula (III'), when A is N, then $T_4$ or $T_{4'}$ is not present and, when B is N, then $T_3$ or $T_{3'}$ is not present; wherein
  $T_3$, $T_{3'}$, $T_4$ and $T_{4'}$ are independently a hydrogen atom; an alkyl group; a cycloalkyl group optionally substituted by an alkyl or alkoxy group; an aryl group optionally substituted by an alkyl or alkoxy group; an alkenyl group; an alkynyl group; or an arylalkyl group, wherein the aryl part is optionally substituted by an alkyl or alkoxy group; or wherein
  $T_3$ and $T_4$ form an aryl together with A and B, when A and B are each a carbon atom, provided that $T_{3'}$ and $T_{4'}$ are not present;
  $T_1$ and $T_2$ are independently an alkyl group; an alkyl group is optionally substituted by an alkyl; an alkyl group, which is perfluorinated or optionally substituted by a perfluoroalkyl group; a cycloalkyl group is optionally substituted by an alkyl or alkoxy group; an aryl group is optionally substituted by an alkyl or alkoxy group; an alkenyl group; an alkynyl group; or an arylalkyl group, wherein the aryl part is optionally substituted by an alkyl or alkoxy group; or

$T_1$ and $T_2$ are independently a monovalent radical of formula (III):

—V1-V2 (III)

wherein
V1 is a saturated or an unsaturated divalent hydrocarbon group, which is optionally substituted,
V2 is a monovalent group selected from the group consisting of:
alkoxy, —OR$^a$, with R$^a$ corresponding to hydrogen, alkyl or aryl;
silyl, —Si(OR$^b$)$_x$(R$^c$)$_{3-x}$, with R$^b$ corresponding to hydrogen, alkyl, silyl or siloxanyl, R$^c$ corresponding to alkyl, aryl and x being an integer from 0 to 3; and
amine; or
the substituents $T_1$, $T_2$, $T_3$, $T_{3'}$, $T_4$ and $T_{4'}$ form a saturated or an unsaturated hydrocarbon chain, in pairs, when they are located on two adjacent ring members in the formulae (III) and (III');
$Z_1$ is independently an anion derived from a Brönsted; and
collecting said at least one carbene C,
wherein said at least one carbene C has the formula (II) or (II'):

(II)

(II')

2. The process of claim 1, wherein said at least one alcohol has the formula (I°) R°OH, wherein R° is an alkyl, cycloalkyl, aryl, alkenyl, alkynyl, arylalkyl, silyl or siloxane group.

3. The process of claim 1, wherein said strong base is selected from the group consisting of alkali metal and alkaline earth metal hydroxides, alkoxides, hydrides and amides.

4. The process of claim 1, wherein said alcoholic medium is sublimed so as to collect said carbene C in solid form.

5. The process of claim 1, wherein said reacting is at a temperature of from 0° C. to 100° C.

6. The process of claim 1, wherein compound B has said V2 group, and V2 is an amine which is —N(R$^a$)$_2$, with R$^a$ corresponding to hydrogen, alkyl or aryl.

7. The process of claim 1, wherein $Z_1$ is independently an anion derived from a Brönsted acid (protic acid) selected from the group consisting of:
carboxylic acids of formula $G_o$-COOH, wherein $G_o$ is an a $C_1$-$C_{22}$ alkyl; or a $C_6$-$C_{18}$ aryl, substituted by one or more $C_1$-$C_6$ alkyls;
sulfonic acids of formula $G_o$-$SO_3H$;
phosphoric acids of formula $G_o$-$PO_3H$;
the following inorganic acids: HF, HCl, HBr, HI, $H_2SO_4$, $H_3PO_4$, $HClO_4$ and $HBF_4$, taken by themselves alone or in a combination thereof;
and mixtures thereof.

8. The process of claim 2, wherein R° is selected from the group consisting of: methyl, ethyl, propyl and butyl.

9. The process of claim 1, wherein said strong base is selected from the group consisting of $CH_3ONa$, potassium tert-butoxide, KOH, NaOH, $CH_3CH_2OMgOCH_2CH_3$, and mixtures thereof.

10. The process of claim 1, wherein compound B has said V1 group which is a linear or branched $C_1$-$C_{10}$ alkylene.

11. The process of claim 1, wherein said compound B is compound (III).

12. The process of claim 1, wherein said compound B is compound (III').

13. The process of claim 1, wherein the at least one alcohol is isopropanol.

14. The process of claim 13, wherein the mole ratio of the isopropanol to the compound B is greater than about 27.

15. The process of claim 1, wherein the at least one alcohol is ethanol.

16. The process of claim 15, wherein the mole ratio of the ethanol to the compound B is greater than about 27.

* * * * *